United States Patent
Kaye et al.

(10) Patent No.: US 11,654,140 B2
(45) Date of Patent: May 23, 2023

(54) TREATMENT OF OCULAR INFLAMMATORY DISEASES USING LAQUINIMOD

(71) Applicant: Active Biotech AB, Lund (SE)

(72) Inventors: Joel Kaye, Netanya (IL); Hussein Hallak, East Jerusalem (IL); Nora Tarcic, Modiin (IL)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 15/816,402

(22) Filed: Nov. 17, 2017

(65) Prior Publication Data

US 2018/0071275 A1 Mar. 15, 2018

Related U.S. Application Data

(63) Continuation of application No. 15/670,684, filed on Aug. 7, 2017, now abandoned, which is a continuation of application No. 15/582,162, filed on Apr. 28, 2017, now abandoned, which is a continuation of application No. 13/909,403, filed on Jun. 4, 2013, now abandoned.

(60) Provisional application No. 61/655,526, filed on Jun. 5, 2012.

(51) Int. Cl.
*A61K 31/4704* (2006.01)
*A61K 9/08* (2006.01)
*A61K 9/00* (2006.01)

(52) U.S. Cl.
CPC ........ *A61K 31/4704* (2013.01); *A61K 9/0048* (2013.01); *A61K 9/0053* (2013.01); *A61K 9/08* (2013.01)

(58) Field of Classification Search
CPC ........ A61K 31/4704; A61K 9/00; A61K 9/08; A61K 9/0053; A61K 9/0048
See application file for complete search history.

(56) References Cited

U.S. PATENT DOCUMENTS

| | | | |
|---|---|---|---|
| 3,024,257 A | 3/1962 | Millar et al. |
| 4,107,310 A | 8/1978 | Allais et al. |
| 4,547,511 A | 10/1985 | Eriksoo et al. |
| 4,628,053 A | 12/1986 | Fries et al. |
| 4,738,971 A | 4/1988 | Eriksoo et al. |
| 5,716,638 A | 2/1998 | Touitou |
| 5,912,349 A | 6/1999 | Sih |
| 6,077,851 A | 6/2000 | Bjork et al. |
| 6,121,287 A | 9/2000 | Bjork et al. |
| 6,133,285 A | 10/2000 | Bjork et al. |
| 6,307,050 B1 | 10/2001 | Kwiatkowski et al. |
| 6,395,750 B1 | 5/2002 | Hedlund et al. |
| 6,593,343 B2 | 7/2003 | Bjork et al. |
| 6,605,616 B1 | 8/2003 | Bjork et al. |
| 6,696,407 B1 | 2/2004 | Longo et al. |
| 6,802,422 B2 | 10/2004 | Kalvelage et al. |
| 6,875,869 B2 | 4/2005 | Jansson |
| 7,485,311 B2 | 2/2009 | Lue et al. |
| 7,560,100 B2 | 7/2009 | Pinchasi et al. |
| 7,560,557 B2 | 7/2009 | Jansson |
| 7,589,208 B2 | 9/2009 | Jansson et al. |
| 7,884,208 B2 | 2/2011 | Frenkel et al. |
| 7,989,473 B2 | 8/2011 | Patashnik et al. |
| 8,178,127 B2 | 5/2012 | Safadi et al. |
| 8,252,933 B2 | 8/2012 | Gant et al. |
| 8,314,124 B2 | 11/2012 | Jansson et al. |
| 8,383,645 B2 | 2/2013 | Patashnik |
| 8,975,279 B2 | 3/2015 | Frenkel et al. |
| 2002/0173520 A1 | 11/2002 | Bjork et al. |
| 2003/0087929 A1 | 5/2003 | Kimura et al. |
| 2003/0119826 A1 | 6/2003 | Manning et al. |

(Continued)

FOREIGN PATENT DOCUMENTS

| | | |
|---|---|---|
| EP | 1073639 | 12/2002 |
| EP | 1097139 | 12/2002 |

(Continued)

OTHER PUBLICATIONS

PCT International Search Report dated Nov. 5, 2013 in connection with PCT International Application No. PCT/US13/44058.
Written Opinion of the International Searching Authority dated Nov. 5, 2013 in connection with PCT International Application No. PCT/US13/44058.
Mintz, R et al. (2004) "Ocular Manifestations of Inflammatory Bowel Disease" Inflamm Bowel Dis, Mar. 2004, 10(2):135-139.
Reagan-Shaw et al. (2007) "Dose translation from animal to human studies revisited" FASEB J 22:659-661.

(Continued)

*Primary Examiner* — Michael G. Hartley
*Assistant Examiner* — Danielle Sullivan
(74) *Attorney, Agent, or Firm* — James S. Keddie; Bozicevic, Field & Francis LLP

(57) ABSTRACT

Disclosed is a method for treating an ocular inflammatory disease (OID), e.g., uveitis or conjunctivitis, comprising periodic administration of a therapeutically effective amount of laquinimod or a pharmaceutically acceptable salt thereof. Also provided is a pharmaceutical composition comprising laquinimod or a pharmaceutically acceptable salt thereof for use in treating a subject suffering from an OID, uveitis, bacterial conjunctivitis, viral conjunctivitis, an inflammation of the orbital tissue, the lacrimal apparatus, the eyelid, the cornea, the retina or the optic pathway. This application also provides a method for treating a subject suffering from an autoimmune disease-associated ocular inflammation comprising periodic ocular administration to the subject a therapeutically effective amount of laquinimod or a pharmaceutically acceptable salt, and an ocular pharmaceutical composition comprising laquinimod or a pharmaceutically acceptable salt thereof for use in treating an autoimmune disease-associated ocular inflammation.

25 Claims, No Drawings

(56) References Cited

U.S. PATENT DOCUMENTS

| | | |
|---|---|---|
| 2003/0124187 A1 | 7/2003 | Mention et al. |
| 2004/0247673 A1 | 12/2004 | Fergione et al. |
| 2005/0074451 A1 | 4/2005 | Yednock et al. |
| 2005/0192315 A1 | 9/2005 | Jansson et al. |
| 2005/0215586 A1 | 9/2005 | Jansson et al. |
| 2005/0250681 A1 | 11/2005 | Molina |
| 2005/0271717 A1 | 12/2005 | Berchielli et al. |
| 2006/0004019 A1 | 1/2006 | Lieberburg |
| 2007/0086979 A1 | 4/2007 | Chevrier et al. |
| 2007/0207141 A1 | 9/2007 | Lieberburg |
| 2007/0231319 A1 | 10/2007 | Yednock |
| 2007/0280891 A1 | 12/2007 | Tamarkin et al. |
| 2008/0044382 A1 | 2/2008 | Lieberburg |
| 2008/0063607 A1 | 3/2008 | Tamarkin et al. |
| 2008/0090897 A1 | 4/2008 | Steiner et al. |
| 2008/0108641 A1 | 5/2008 | Ajami |
| 2008/0118553 A1 | 5/2008 | Frenkel et al. |
| 2008/0166348 A1 | 7/2008 | Kupper et al. |
| 2008/0206159 A1 | 8/2008 | Tamarkin et al. |
| 2009/0048181 A1 | 2/2009 | Schipper et al. |
| 2009/0062330 A1 | 3/2009 | Kalafer et al. |
| 2009/0081259 A1 | 3/2009 | Jonas et al. |
| 2009/0148462 A1 | 6/2009 | Chevrier et al. |
| 2009/0156542 A1 | 6/2009 | Purschke et al. |
| 2009/0221575 A1 | 9/2009 | Gerber et al. |
| 2010/0168099 A1 | 7/2010 | Falco et al. |
| 2010/0322900 A1 | 12/2010 | Tarcic et al. |
| 2011/0027219 A1* | 2/2011 | Tarcic .............. A61K 45/06 424/85.1 |
| 2011/0034508 A1 | 2/2011 | Hayardeny |
| 2011/0112141 A1 | 5/2011 | Frenkel |
| 2011/0118308 A1 | 5/2011 | Frenkel et al. |
| 2011/0217295 A1 | 9/2011 | Haviv et al. |
| 2011/0218179 A1 | 9/2011 | Haviv et al. |
| 2011/0218203 A1 | 9/2011 | Kaye et al. |
| 2011/0251235 A1 | 10/2011 | Patashnik |
| 2012/0009226 A1* | 1/2012 | Dixit .............. A61P 3/10 424/400 |
| 2012/0010238 A1 | 1/2012 | Piryatinsky et al. |
| 2012/0010239 A1 | 1/2012 | Fristedt |
| 2012/0142730 A1 | 6/2012 | Tarcic et al. |
| 2012/0225124 A1 | 9/2012 | Safadi et al. |
| 2012/0302600 A1 | 11/2012 | Patashnik et al. |
| 2013/0028866 A1 | 1/2013 | Gilgun et al. |
| 2013/0029916 A1 | 1/2013 | Gilgun et al. |
| 2013/0045886 A1 | 2/2013 | Whittaker et al. |
| 2013/0096158 A1 | 4/2013 | Hallak et al. |
| 2013/0184310 A1 | 7/2013 | Haviv et al. |
| 2013/0203807 A1 | 8/2013 | Tarcic et al. |
| 2013/0217724 A1 | 8/2013 | Ioffe et al. |
| 2013/0259856 A1 | 10/2013 | Kaye |
| 2013/0272996 A1 | 10/2013 | Tarcic et al. |
| 2013/0303569 A1 | 11/2013 | Bar-Zohar et al. |
| 2013/0345256 A1 | 12/2013 | Laxer |
| 2013/0345257 A1 | 12/2013 | Hahn et al. |
| 2014/0017266 A1 | 1/2014 | Tarcic et al. |
| 2014/0018386 A1 | 1/2014 | Sarfati et al. |
| 2014/0024678 A1 | 1/2014 | Safadi et al. |
| 2014/0045887 A1 | 2/2014 | Martino |
| 2014/0051723 A1 | 2/2014 | Piryatinsky et al. |
| 2014/0057883 A1 | 2/2014 | Tarcic et al. |
| 2014/0105850 A1 | 4/2014 | Tarcic et al. |
| 2014/0107154 A1 | 4/2014 | Filippi |
| 2014/0128430 A1 | 5/2014 | Frenkel |
| 2014/0171647 A1 | 6/2014 | Frenkel et al. |

FOREIGN PATENT DOCUMENTS

| | | |
|---|---|---|
| EP | 1095021 | 9/2003 |
| EP | 1511732 | 12/2006 |
| EP | 17320531 | 4/2011 |
| WO | 1999055678 | 11/1999 |
| WO | 2000003991 | 1/2000 |
| WO | 2000003992 | 1/2000 |
| WO | 2003106424 | 12/2003 |
| WO | 20050774899 | 8/2005 |
| WO | 2007146248 | 12/2007 |
| WO | 2007146331 | 12/2007 |
| WO | 2008085484 | 7/2008 |
| WO | WO 2010001257 A2 | 1/2010 |
| WO | 2010102826 | 9/2010 |
| WO | 2011084473 | 7/2011 |
| WO | 2012001647 | 1/2012 |
| WO | 2012078591 | 6/2012 |

OTHER PUBLICATIONS

"Guidance for Industry = Estimating the Maximum Safe . . . Volunteers" U.S. Department of Health and Human Services, FDA, Center for Drugs Evaluation and Research, date Jul. 2005.

PCT International Preliminary Report on Patentability dated Jan. 31, 2012 in connection with PCT International Applicatino No. PCT/US2010/002129 filed Jul. 29, 2010.

PCT International Preliminary Report dated Sep. 7, 2010 in connection with PCT International Application No. PCT/US2010/002129 filed Jul. 29, 2010.

Written Opinion of the International Searching authority dated Sep. 7, 2010 in connection with PCT International Application No. PCT/US2010/02129 filed Jul. 29, 2010.

Supplementary European Search Report dated Jan. 10, 2013 in connection with European Patent Application No. 10804826.5.

ClinicalTrials.gov (2008) "Laquinimod Phase IIa Study in Active Crohn's Disease". . . <http:www/clinicaltrials.gov/ct2/show/NCT00737832?term=Crohns&recr=Open&rank=2>.

EMEA, (2001) "Points to consider on clinical investigation of medicincal products for the management of Crohn's disease", CPMP/EWP/2284/99 Rev.1.

EMEA, (2008) "Guideline on the Development of the New Medicinal Product For the Treatment of Crohn's Disease", CPMP/EWP/2284/99 Rev. 1.

Friedman et al., (2001) "Inflammatory Bowel Disease", Harrison's Priniciples of Internal Medicine, New York, McGraw-Hill Professional, 2001: 1679-92.

Guindi and Ridell, (2004) "Indeterminate Colitis", Journal of Clinical Pathology, 54:1233-44.

Hendrickson et al., (2002) "Clinical aspects adn pathophysiology of inflammatory bowel disease", Clin. Microbiol. Rev. 15:79-94.

Wen et al., (2004) "Inflammatory bowel disease: autoimmune or immune-mediated pathogenesis?", Clin. Develop. Immunol., 11:195-204.

Wu et al., (2010) "Crohns Disease", Emedicine, updated Mar. 17, 2010, retrieved from Jul. 27, 2010, available from http://emedicine.medscape.com/article/172940-overview.

Bertelmann and Pleyer (2004) Immunomodulatory Therapy in Opthalmology—Is There a Place for Topical Application? Opthalmogica; Nov./Dec. 2004; 218, 6 pg 359-367.

Mishra et al. (2011) "Recent Patents and Emerging Therapeutics in the Treatment of Allergic Conjuctivitis" Recent Pat Inflamm Allergy Drug Discov. Jan. 2011; 5(1): 26-36.

Foster, C. Stephen (2003) "Ocular Inflammatory Disease: The importance of Aggressive Therapy" Medscape, CME Released: Dec. 17, 2003; Valid for credit through Dec. 17, 2004.

Girouard et al. (2011) "Guiding Patient Decisions Concerning Oral Therapies" MS Scan—Your Eye on the MS Literature, Issue 30, pp. 1-3.

Caspi, "A look at autoimmunity and inflammation in the eye", The Journal of Clinical Investigation, Sep. 2010, 120(9): 3073-3083.

Gaudana et al., "Ocular Drug Delivery", The AAPS Journal, Sep. 2010, 12(3): 348-360.

Gote et al., "Ocular Drug Delivery: Present Innovations and Future Challenges", The Journal of Pharmacology and Experimental Therapeutics, Sep. 2019, 370: 602-624.

(56) References Cited

OTHER PUBLICATIONS

Hosoya et al., "Strategies for therapy of rentinal diseases using systemic drug delivery: relevance of transporters at the blood—retinal barrier", Expert Opin. Drug Deliv., 2011, 8(12): 1571-1587.
Patel et al., "Ocular drug delivery systems: An overview", World J Pharmacol., 2013, 2(2): 47-64.
Singh et al., "The Paradigm of Th1 and Th2 Cytokines", Immunologic Research, 1999, 20: 147-161.

* cited by examiner

TREATMENT OF OCULAR INFLAMMATORY DISEASES USING LAQUINIMOD

This application is a continuation of U.S. Ser. No. 15/760,684, filed Aug. 7, 2017, which is a continuation of U.S. Ser. No. 15/582,162, filed Apr. 28, 2017, a continuation of U.S. Ser. No. 13/909,403, filed Jun. 4, 2013, which claims benefit of U.S. Provisional Application No. 61/655,526, filed Jun. 5, 2012, the entire contents of each of which are hereby incorporated by reference in their entirety into this application.

Throughout this application, various publications are referenced. The disclosures of these publications in their entireties are hereby incorporated by reference into this application in order to more fully describe the state of the art to which this invention pertains.

BACKGROUND OF THE INVENTION

Ocular Inflammatory Disease ("OID") is a general term for describing inflammation affecting one or more parts of the eye or surrounding eye tissue. Uveitis is the inflammation of the uvea or the uveal tract, which includes the iris, the ciliary body and the choroid portions of the eye. Inflammation of the overlying retina, called retinitis, or of the optic nerve, called optic neuritis, may occur with or without accompanying uveitis. Anatomically, uveitis may be classified as anterior, intermediate, posterior or diffuse, depending on the portion of the uveal tract that is affected. Anterior uveitis is localized primarily to the anterior segment of the eye and includes iritis and iridocyclitis. Intermediate uveitis, also called peripheral uveitis, is centered in the area immediately behind the iris and lens in the region of the ciliary body and pars plana, hence the alternate terms "cyclitis' and "pars planitis." Posterior uveitis signifies any of a number of forms of retinitis, choroiditis, or optic neuritis. Diffuse uveitis implies inflammation involving all parts of the eye, including anterior, intermediate, and posterior structures (The Merck Manual, 1999).

Inflammation from uveitis may result in a variety of other eye conditions, including glaucoma, cataracts, and cystoid macular edema, and ultimately may lead to permanent vision loss. Uveitis is the third leading cause of blindness in the developed world. There is no one root cause of uveitis or other OID. Causes range from infections by certain bacteria, parasites, fungus, and viruses; trauma; autoimmune disease; inducement by certain drugs such as bisphosphonates or sulfaonamides; and inducement by certain malignant cancers such as lymphoma.

Conjunctivitis is another OID that causes inflammation of the conjunctival tissue. The conjunctiva is the thin, transparent layer of tissue that covers the outside surface of the eye, including the cornea and the visible sclera (the white part of the eye), and also lines the eyelids. The conjunctiva secretes oils and mucus and is responsible for moistening and lubricating the eye. There are several types of conjunctivitis, some more severe than others. Seasonal and perennial allergic conjunctivitis (SAC and PAC) are generally associated with allergic reactions. The more severe vernal and atopic keratoconjunctivitis (VKC and AKC) are also associated with hypersensitivity to an allergen, but inflammation occurs in both the conjunctiva and the cornea. VKC is intermittent and often occurs seasonally, most commonly in summer, while AKC does not have a seasonal component. Symptoms of SAC and PAC include itching, swelling and tearing while symptoms for VKC and AKC are more severe and include pain, visual loss and corneal scarring.

Generally, allergic eye reactions such as that caused by OID consist of two different phase reactions, early-phase reaction and late phase reaction, and each reaction has different cell types considered to be the major effector cells for production of the eye disease. Early-phase reaction, which occurs with SAC and PAC, for example, involves mast cells as the major effector cells, while late-phase reaction, which occurs with VKC and AKC, for example, involves eosinophils as the major effector cells.

Current therapies for allergic conjunctivitis include anti-allergics with antihistamine and mast cell stabilizing functions for treatment of SAC, steroids for PAC, and steroids and/or cyclosporine A for AKC and VKC. There is a need for additional treatment of OID.

SUMMARY OF THE INVENTION

Disclosed is a method of treating ocular inflammatory disease (OID), including uveitis and conjunctivitis, using laquinimod or a pharmaceutically acceptable salt thereof. Laquinimod is a novel synthetic compound with high oral bioavailability, which has been suggested as an oral formulation for Relapsing Remitting Multiple Sclerosis (RRMS). Laquinimod and its sodium salt form are described, for example, in U.S. Pat. No. 6,077,851.

This application provides a method of treating a subject suffering from an ocular inflammatory disease (OID), the method comprising periodic administration to the subject of a therapeutically effective amount of laquinimod or a pharmaceutically acceptable salt thereof effective to treat the subject.

This application also provides a pharmaceutical composition comprising laquinimod or a pharmaceutically acceptable salt thereof for use in treating a subject suffering from an ocular inflammatory disease.

This application also provides a pharmaceutical composition comprising laquinimod or a pharmaceutically acceptable salt thereof for use in treating a subject suffering from uveitis, bacterial conjunctivitis, viral conjunctivitis, or an inflammation of the orbital tissue, the lacrimal apparatus, the eyelid, the cornea, the retina or the optic pathway.

This application also provides a pharmaceutical composition for use in treating a subject suffering from allergic conjunctivitis or uveitis comprising a unit dose of 10 µL of an aqueous pharmaceutical solution which contains in solution at least 0.2 mg laquinimod or a pharmaceutically acceptable salt thereof.

This application also provides a method of treating a subject suffering from an autoimmune disease-associated ocular inflammation, the method comprising periodic ocular administration to the subject a therapeutically effective amount of laquinimod or a pharmaceutically acceptable salt thereof effective to treat the subject.

This application also provides an ocular pharmaceutical composition comprising laquinimod or a pharmaceutically acceptable salt thereof for use in treating an autoimmune disease-associated ocular inflammation.

DETAILED DESCRIPTION OF THE INVENTION

This application provides for a method of treating a subject suffering from an ocular inflammatory disease (OID), the method comprising periodic administration to the subject of a therapeutically effective amount of laquinimod or a pharmaceutically acceptable salt thereof effective to treat the subject.

In one embodiment, the ocular inflammatory disease is uveitis, bacterial conjunctivitis, viral conjunctivitis, or an inflammation of the orbital tissue, the lacrimal apparatus, the eyelid, the cornea, the retina or the optic pathway. In an embodiment, the OID is conjunctivitis. In another embodiment, the conjunctivitis is bacterial conjunctivitis. In yet another embodiment, the conjunctivitis is viral conjunctivitis.

In one embodiment, the OID is uveitis. In another embodiment, the uveitis is anterior uveitis. In another embodiment, the uveitis is intermediate uveitis. In another embodiment, the uveitis is posterior uveitis. In yet another embodiment, the uveitis is diffuse uveitis.

In one embodiment, the therapeutically effective amount of laquinimod a pharmaceutically acceptable salt thereof is effective to reduce a symptom of the ocular inflammatory disease in the subject, induce clinical response, induce or maintain clinical remission, inhibit disease progression, inhibit a disease complication, reduce intraocular inflammation or reduce retina tissue destruction in the subject. In another embodiment, the therapeutically effective amount of laquinimod or pharmaceutically acceptable salt thereof is effective to reduce one or more symptoms of the OID in the subject. In another embodiment, the therapeutically effective amount of laquinimod or pharmaceutically acceptable salt thereof is effective to reverse the progression of the OID. In another embodiment, the therapeutically effective amount of laquinimod or pharmaceutically acceptable salt thereof is effective to induce a clinical response or induce or maintain clinical remission in the subject suffering from the OID. In another embodiment, the therapeutically effective amount of laquinimod or pharmaceutically acceptable salt thereof is effective to inhibit disease progression or disease complication in the subject suffering from the OID. In another embodiment, the therapeutically effective amount of laquinimod or pharmaceutically acceptable salt thereof is effective to decrease eosinophil infiltration at the site of inflammation. In another embodiment, the therapeutically effective amount of laquinimod or pharmaceutically acceptable salt thereof is effective to reduce intraocular inflammation. In yet another embodiment, the therapeutically effective amount of laquinimod or pharmaceutically acceptable salt thereof is effective to reduce retina tissue destruction in the subject.

In one embodiment of the present invention, the OID is conjunctivitis and the therapeutically effective amount of laquinimod or pharmaceutically acceptable salt thereof is effective to reduce a symptom of conjunctivitis in the subject. In another embodiment of the present invention, the OID is uveitis and the therapeutically effective amount of laquinimod or pharmaceutically acceptable salt thereof is effective to reduce a symptom of uveitis in the subject. In yet another embodiment of the present invention, the ocular inflammatory disease is an inflammation of the orbital tissue, the lacrimal apparatus, the eyelid, the cornea, the retina or the optic pathway and the therapeutically effective amount of laquinimod or pharmaceutically acceptable salt thereof is effective to reduce a symptom of the inflammation in the subject.

In one embodiment, the laquinimod or pharmaceutically acceptable salt thereof is administered topically. In another embodiment, administration of the laquinimod or pharmaceutically acceptable salt thereof is ocular administration. In another embodiment, administration of the laquinimod or pharmaceutically acceptable salt thereof is oral administration. In another embodiment the periodic administration is local administration. In another embodiment, the laquinimod or pharmaceutically acceptable salt thereof is administered to the affected eye of the subject.

In one embodiment, the laquinimod or pharmaceutically acceptable salt thereof is administered in the form of a liquid or a gel. In another embodiment, the laquinimod or pharmaceutically acceptable salt thereof is administered in liquid form. In another embodiment, the laquinimod or pharmaceutically acceptable salt thereof is administered in a liquid eye drop. In another embodiment, the laquinimod or pharmaceutically acceptable salt thereof is administered in gel form.

In one embodiment, the concentration of laquinimod or pharmaceutically acceptable salt thereof in the liquid or gel is 0.5% (5 mg/ml)-10.0% (100 mg/ml). In another embodiment, the concentration of laquinimod or pharmaceutically acceptable salt thereof is 1.0% (10 mg/ml)-7.0% (70 mg/ml). In another embodiment, the concentration of laquinimod or pharmaceutically acceptable salt thereof is 1.0% (10 mg/ml)-5.0% (50 mg/ml). In another embodiment, the concentration of laquinimod or pharmaceutically acceptable salt thereof is about 1.0% (10 mg/ml). In another embodiment, the concentration of laquinimod or pharmaceutically acceptable salt thereof is about 5.0% (50 mg/ml). In an embodiment, the volume of liquid or gel per administration is about 10 µl. As used herein "mg/ml" designates the amount (mg) of laquinimod or pharmaceutically acceptable salt thereof per volume (ml) of solution.

In another embodiment, the therapeutically effective amount of laquinimod or pharmaceutically acceptable salt thereof is 0.05-4.0 mg per administration. In another embodiment, the therapeutically effective amount of laquinimod or pharmaceutically acceptable salt thereof is 0.05-2.0 mg per administration. In another embodiment, the therapeutically effective amount of laquinimod or pharmaceutically acceptable salt thereof is about 0.1 mg per administration. In another embodiment, the therapeutically effective amount of laquinimod or pharmaceutically acceptable salt thereof is about 0.5 mg per administration. In yet another embodiment, the therapeutically effective amount of laquinimod or pharmaceutically acceptable salt thereof is at least 0.02 mg/day.

In an embodiment, the periodic administration is 1-5 times a day. In one embodiment, the periodic administration is once a day. In another embodiment, the periodic administration is twice a day. In another embodiment, the periodic administration is three times a day. In yet another embodiment, the periodic administration is once every 2 days.

In an embodiment of the invention, the laquinimod or pharmaceutically acceptable salt thereof is administered once daily for a period of 2 to 14 days. In another embodiment, the laquinimod or pharmaceutically acceptable salt thereof is administered once daily for a period of 5 to 14 days. In another embodiment, the laquinimod or pharmaceutically acceptable salt thereof is administered once daily for a period of 10 to 14 days. In another embodiment, the laquinimod or pharmaceutically acceptable salt thereof is administered once daily for about 7 days.

In an embodiment of the present invention, the ocular inflammatory disease is uveitis and the therapeutically effective amount of laquinimod or pharmaceutically acceptable salt thereof is at least 0.2 mg/day.

In another embodiment of the present invention, the ocular inflammatory disease is allergic conjunctivitis and the therapeutically effective amount of laquinimod or pharmaceutically acceptable salt thereof is at least 0.2 mg/day. In another embodiment, the OID is seasonal allergic conjunctivitis (SAC) or perennial allergic conjunctivitis (PAC). In another embodiment, the OID is atopic keratoconjunctivitis (AKC) or vernal keratoconjunctivitis (VKC).

In one embodiment, the therapeutically effective amount of laquinimod or pharmaceutically acceptable salt thereof is effective to reduce a symptom of the conjunctivitis in the subject. In another embodiment, the therapeutically effective amount of laquinimod or pharmaceutically acceptable salt thereof is effective to inhibit late ocular anaphylaxis in the subject. In another embodiment, the therapeutically effective amount of laquinimod or pharmaceutically acceptable salt thereof is effective to reduce eosinophil infiltration in to the conjunctiva of the subject. In yet another embodiment, the eosinophil infiltration into the conjunctiva is measured by eosinophil density in the conjunctiva.

In one embodiment, the eosinophil density is reduced by at least 40% as compared to a subject not administered laquinimod or pharmaceutically acceptable salt thereof. In another embodiment, the eosinophil density is reduced by at least 45% as compared to a subject not administered laquinimod or pharmaceutically acceptable salt thereof. In another embodiment, the eosinophil density is reduced by at least 50% as compared to a subject not administered laquinimod or pharmaceutically acceptable salt thereof. In another embodiment, the eosinophil density is reduced by at least 55% as compared to a subject not administered laquinimod or pharmaceutically acceptable salt thereof. In another embodiment, the eosinophil density is reduced by at least 60% as compared to a subject not administered laquinimod or pharmaceutically acceptable salt thereof. In yet another embodiment, the eosinophil density is reduced by at least 65% as compared to a subject not administered laquinimod or pharmaceutically acceptable salt thereof.

In one embodiment, the laquinimod or pharmaceutically acceptable salt thereof is administered topically. In another embodiment, administration of the laquinimod or pharmaceutically acceptable salt thereof is ocular administration. In another embodiment, administration of the laquinimod or pharmaceutically acceptable salt thereof is oral administration. In another embodiment the periodic administration is local administration. In another embodiment, the laquinimod or pharmaceutically acceptable salt thereof is administered to the affected eye of the subject.

In one embodiment, the laquinimod or pharmaceutically acceptable salt thereof is administered in the form of a liquid or a gel. In another embodiment, the laquinimod or pharmaceutically acceptable salt thereof is administered in liquid form. In another embodiment, the laquinimod or pharmaceutically acceptable salt thereof is administered in a liquid eye drop. In another embodiment, the laquinimod or pharmaceutically acceptable salt thereof is administered in gel form.

In one embodiment, the concentration of laquinimod or pharmaceutically acceptable salt thereof in the liquid or gel is 2.0% (20 mg/ml)-10.0% (100 mg/ml). In another embodiment, the concentration of laquinimod or pharmaceutically acceptable salt thereof is 2.0% (20 mg/ml)-7.0% (70 mg/ml). In another embodiment, the concentration of laquinimod or pharmaceutically acceptable salt thereof is 2.0% (20 mg/ml)-5.0% (50 mg/ml). In another embodiment, the concentration of laquinimod or pharmaceutically acceptable salt thereof is about 5.0% (50 mg/ml). In an embodiment, the volume of liquid or gel per administration is about 10 µl. As used herein "mg/ml" designates the amount (mg) of laquinimod or pharmaceutically acceptable salt thereof per volume (ml) of solution.

In one embodiment, the therapeutically effective amount of laquinimod or pharmaceutically acceptable salt thereof is 0.2-4.0 mg per administration. In another embodiment, the therapeutically effective amount of laquinimod or pharmaceutically acceptable salt thereof is 0.2-2.0 mg per administration. In yet another embodiment, the therapeutically effective amount of laquinimod or pharmaceutically acceptable salt thereof is about 0.5 mg per administration.

In an embodiment, the periodic administration is 1-5 times a day. In one embodiment, the periodic administration is once a day. In another embodiment, the periodic administration is twice a day. In another embodiment, the periodic administration is three times a day. In yet another embodiment, the periodic administration is once every 2 days.

In an embodiment of the invention, the laquinimod or pharmaceutically acceptable salt thereof is administered once daily for a period of 2 to 14 days. In another embodiment, the laquinimod or pharmaceutically acceptable salt thereof is administered once daily for a period of 5 to 14 days. In another embodiment, the laquinimod or pharmaceutically acceptable salt thereof is administered once daily for a period of 10 to 14 days. In another embodiment, the laquinimod or pharmaceutically acceptable salt thereof is administered once daily for about 7 days.

In one embodiment, the laquinimod or pharmaceutically acceptable salt thereof is in a pharmaceutical composition which comprises a pharmaceutically acceptable carrier. In another embodiment, the pharmaceutical composition is in the form of a tablet or capsule. In another embodiment, the pharmaceutical composition is a liquid solution. In another embodiment, the liquid solution is prepared by dissolving laquinimod or a pharmaceutically acceptable salt thereof in a sterile pH-neutral solution. In one embodiment, the pH-neutral solution is saline. In another embodiment, the pH-neutral solution is phosphate buffered saline (PBS). In another embodiment, the pH-neutral solution is sterile water.

In one embodiment, the pharmaceutical composition is a gel. In another embodiment, the pharmaceutically acceptable carrier is hydrophilic. In another embodiment, the pharmaceutically acceptable carrier comprises at least one gelling or suspension agent. Examples of suitable gelling or suspension agents known in the art include carbomers, modified cellulose derivatives, naturally-occurring, synthetic or semi-synthetic gums such as xanthan gum, acacia and tragacanth, modified starches, co-polymers such as those formed between maleic anhydride and methyl vinyl ether, colloidal silica and methacrylate derivatives sold under the trade name EUDRAGIT® (available from Evonik Industries, Essen, Germany) or a mixture thereof. In another embodiment, the pharmaceutically acceptable carrier comprises at least one surfactant or emulsifying agent compatible with any pharmacologically active agents or pharmaceutically acceptable components present. In one embodiment, the surfactants include non-ionic, cationic and anionic surfactants. In another embodiment, the surfactants include non-ionic surfactants such as sorbitan fatty acid esters (SPANS®) and the corresponding polyoxyethylene (POE) adducts (TWEENS®).

In an embodiment, the pharmaceutically acceptable salt of laquinimod includes lithium, sodium, potassium, magnesium, calcium, manganese, copper, zinc, aluminum and iron. Salt formulations of laquinimod and the process for preparing the same are described in, e.g., U.S. Patent Application Publication No. 2005/0192315 and PCT International Application Publication No. WO 2005/074899, each of which is hereby incorporated by reference into this application. In one embodiment, the pharmaceutically acceptable salt of laquinimod is laquinimod sodium.

In an embodiment of the invention, the method comprises topically administering to the affected eye of the subject a 5.0% (50 mg/ml) solution of laquinimod sodium once per day for a period of 14 days. In another embodiment, the method comprises topically administering to the affected eye of the subject a 5.0% (50 mg/ml) solution of laquinimod sodium once per day for a period of 10 days.

In an embodiment, the therapeutically effective amount of laquinimod or pharmaceutically acceptable salt thereof is 1.0-1.5 mg/day. In another embodiment, the therapeutically effective amount of laquinimod or pharmaceutically acceptable salt thereof is 1.2 mg/day. In another embodiment, the therapeutically effective amount of laquinimod or pharmaceutically acceptable salt thereof is at least 0.2 mg/day.

In an embodiment of the invention, the subject is human.

This application also provides for a pharmaceutical composition comprising laquinimod or a pharmaceutically acceptable salt thereof for use in treating a subject suffering from an ocular inflammatory disease.

This application also provides for a pharmaceutical composition comprising laquinimod or a pharmaceutically acceptable salt thereof for use in treating a subject suffering from uveitis, bacterial conjunctivitis, viral conjunctivitis, or an inflammation of the orbital tissue, the lacrimal apparatus, the eyelid, the cornea, the retina or the optic pathway.

This application also provides for a pharmaceutical composition for use in treating a subject suffering from allergic conjunctivitis or uveitis comprising a unit dose of 10 μL of an aqueous pharmaceutical solution which contains in solution at least 0.2 mg laquinimod or a pharmaceutically acceptable salt thereof. In an embodiment, the pharmaceutical composition is an ocular pharmaceutical composition.

This application also provides for a pharmaceutical composition comprising a therapeutically effective amount of laquinimod or a pharmaceutically acceptable salt thereof for use in treating a subject suffering from uveitis, bacterial conjunctivitis, viral conjunctivitis, or an inflammation of the orbital tissue, the lacrimal apparatus, the eyelid, the cornea, the retina or the optic pathway. In an embodiment, the pharmaceutical composition is an ocular pharmaceutical composition.

This application provides for a method of reducing eosinophil density in the conjunctival tissue of a subject comprising periodically administering to the subject an amount of laquinimod or a pharmaceutically acceptable salt thereof effective to reduce the eosinophil density in the conjunctival tissue of the subject.

This application also provides for a method of reducing intraocular inflammation in a subject comprising periodically administering to the subject an amount of laquinimod or a pharmaceutically acceptable salt thereof effective to reduce intraocular inflammation in the subject. This application also provides for a method of reducing retina tissue destruction in a subject comprising periodically administering to the subject an amount of laquinimod or a pharmaceutically acceptable salt thereof effective to reduce retina tissue destruction in the subject. In an embodiment, the amount of laquinimod or pharmaceutically acceptable salt thereof is a therapeutically effective amount. In another embodiment, the administration is ocular administration.

This application also provides for a pharmaceutical composition comprising laquinimod or a pharmaceutically acceptable salt thereof for use in reducing eosinophil density in the conjunctival tissue of a subject or for reducing intraocular inflammation or destruction of retina tissue in a subject. In an embodiment, the pharmaceutical composition comprises a therapeutically effective amount of laquinimod of a pharmaceutically acceptable salt thereof. In another embodiment, the pharmaceutical composition is an ocular pharmaceutical composition.

This application also provides a method of treating a subject suffering from an autoimmune disease-associated ocular inflammation, the method comprising periodic ocular administration to the subject of a therapeutically effective amount of laquinimod or a pharmaceutically acceptable salt thereof effective to treat the subject.

This application also provides an ocular pharmaceutical composition comprising laquinimod or a pharmaceutically acceptable salt thereof for use in treating an autoimmune disease-associated ocular inflammation.

All combinations of the various elements described herein are within the scope of the invention.

Definitions

"Ocular inflammatory diseases" or "OID" as used herein means the inflammation affecting one or more parts of the eye or surrounding eye tissue other than inflammation resulting from an autoimmune disease. OID may include, but is not limited to, inflammation of the orbital tissues, the lacrimal apparatus, the eyelid, the conjunctiva (conjunctivitis), the cornea, the retina, a component of the optic pathway, e.g., the optic nerve, and a component of the uveal tract (uveitis), i.e., the iris, ciliary body and choroid. Specific examples of OID include uveitis, acute conjunctivitis, viral conjunctivitis, nongonococcal bacterial conjunctivitis, adult gonococcal conjunctivitis, inclusion conjunctivitis, seasonal allergic conjunctivitis, chronic conjunctivitis, granular conjunctivitis, perennial allergic conjunctivitis, episcleritis, scleritis, atopic keratoconjunctivitis, and vernal keratoconjunctivitis.

Unlike the use of the term OID herein, the literature may use the term in a less definite manner to refer to ocular inflammation generally, and often including ocular inflammation secondary to an underlying systemic inflammatory disease different from inflammation which represents localized pathologic process without systemic involvement (Gordon, 2006; Rothova et al., 1992; Optometric Clinical Practice Guideline, 2002.) For example, conjunctivitis may result from primary involvement of the conjunctival tissue or may occur secondary to other systemic conditions that produce conjunctival inflammation (Optometric Clinical Practice Guideline, 2002.) In one study conducted by Rothova et al., systemic disease which could be considered to be causally related to ocular inflammation was diagnosed in 26% of the 865 uveitis patients observed (Rothova et al.). However, as used herein OID specifically excludes ocular inflammation which results from an underying, systemic, autoimmune disease.

As used herein "autoimmune disease-associated ocular inflammation" is the inflammation affecting one or more parts of the eye or surrounding eye tissue secondary to an autoimmune disease, and is specifically excluded from the definition of OID herein.

Autoimmune diseases contemplated by the present invention include either cell-mediated disease (e.g., T-cell) or antibody mediated (e.g., B-cell) disorders. Such disorders can be inter alia arthritic conditions, demyelinating diseases and inflammatory diseases. For Example, autoimmune diseases contemplated herein include multiple sclerosis, autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Grave's disease, Guillain-Barre's syndrome, Hashimoto's disease, idiopathic myxedema, myasthenia gravis, psoriasis, pemphigus vulgaris, rheumatoid arthritis, and systemic lupus erythematosus.

"Administering to the subject" means the giving of, dispensing of, or application of medicines, drugs, or remedies to a subject to relieve, cure, or reduce the symptoms associated with a condition, e.g., a pathological condition. The route of administration can be, e.g., topical. Routes of administration can also be classified by whether the effect is local (e.g., in topical administration) or systemic (e.g., in enteral or parenteral administration). "Local administration" as used herein shall mean administration of a compound or composition directly to where its action is desired, and specifically excludes systemic administration. "Topical administration" of a compound or composition as used herein shall mean application of the compound or composition to body surfaces such as the skin or mucous membranes such as eyes. "Ocular administration" as used herein shall mean application of a compound or composition to the eye of a subject or to the skin around the eye (periocular skin) of a subject, i.e., local administration. Examples of ocular administration include topical administration directly to the eye, topical application to the eye lid or injection into a portion of the eye or eye socket. In addition, an "ocular pharmaceutical composition" as used herein means a pharmaceutical composition formulated for ocular administration.

An "amount" or "dose" of laquinimod as measured in milligrams refers to the milligrams of laquinimod acid present in a preparation, regardless of the form of the preparation.

"Unit dose" as used herein is the amount of a compound or composition to be administered to the subject in a single administration. The unit dose disclosed herein can be administered once daily, twice daily, three times daily, four times daily, five times daily, every other day, weekly, twice weekly, three times weekly, four times weekly, five times weekly or six times weekly.

"About" in the context of a numerical value or range means±10% of the numerical value or range recited or claimed.

As used herein, "treating" encompasses, e.g., inducing inhibition, regression, or stasis of a disease, disorder or condition, or ameliorating or alleviating a symptom of a disease, disorder or condition. "Ameliorating" or "alleviating" a condition or state as used herein shall mean to relieve or lessen the symptoms of that condition or state. "Inhibition" of disease progression or disease complication in a subject as used herein means preventing or reducing the disease progression and/or disease complication in the subject.

As used herein, "effective" as in an amount effective to achieve an end, i.e., "therapeutically effective amount", means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to reduce inflammation. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

A "salt" is salt of the instant compounds which have been modified by making acid or base salts of the compounds. The term "pharmaceutically acceptable salt" in this respect, refers to the relatively non-toxic, inorganic and organic acid or base addition salts of compounds of the present invention. A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Pat. No. 7,589,208 and PCT International Application Publication No. WO 2005/074899, which are hereby incorporated by reference into this application.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for topical administration. Laquinimod can be administered alone but is generally mixed with a pharmaceutically acceptable carrier. As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

General techniques and compositions for making dosage forms useful in the present invention are described in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds).; Modern Pharmaceutics Drugs and the Pharmaceutical Sciences, Vol. 40 (Gilbert S. Banker, Christopher T. Rhodes, Eds). These references in their entireties are hereby incorporated by reference into this application.

It is understood that where a parameter range is provided, all integers within that range, including tenths thereof, are also provided by the invention. For example, "5-10%" includes 5.0%, 5.1%, 5.2%, 5.3%, 5.4% etc. up to 10.0%.

Immunomodulatory agents have been suggested for treating certain ocular inflammatory diseases (Foster 2003; Mishra 2011; Shah 1992). However, not all immunomodulatory agents are appropriate for OID. For example, fingolimod (Gilenya® from Novartis AG), an immunomodulatory agent, is known to pose a risk of macular edema in patients with a history of uveitis. (Sergott, 2011) The effects of laquinimod on OID have not been previously reported.

In addition, in accordance with the present invention, a therapeutically effective amount of laquinimod or a pharmaceutically acceptable salt thereof is delivered to a subject via ocular administration. As discussed in Example 2 to follow, not all amounts of laquinimod or a pharmaceutically acceptable salt thereof are "therapeutically effective amounts". A therapeutically effective amount or means for determining a therapeutically effective amount for ocular/local administration of laquinimod have not been previously reported.

This invention will be better understood by reference to the Experimental Examples which follow, but those skilled in the art will readily appreciate that the specific experiments detailed are only illustrative of the invention as described more fully in the claims which follow thereafter.

EXPERIMENTAL EXAMPLES

Example 1: Evaluation of Efficacy Following Daily Topical Administration of Laquinimod in S-Antigen-Induced Experimental Autoimmune Uveitis in Rats (EAU Model)

General.

A 1% (10 mg/ml) and a 5% (50 mg/ml) solution of laquinimod sodium were prepared in sterile water. Dissolution of laquinimod powder was achieved by shaking, stirring, or low-speed vortex. The solutions were stored for up to 2 weeks at 2-8° C. and up to 24 hours at room temperature. Laquinimod solutions were prepared under light protection and were protected from light for the duration of the experiment. Cyclosporine A was used as a reference material at a concentration of 25 mg/kg/j (Fluka). One 100 mg/4 ml in olive oil dose was prepared every 2 days and stored at room temperature.

Animals and Animal Husbandry.

Thirty two (32) female albino Lewis rats, approximately 8 weeks old, were used for this study. All rats were held in observation for at least 3 days to monitor for signs of ill health or ocular abnormalities. Only healthy animals were accepted for use in this study. The rats were housed under identical environmental conditions, with a relative humidity of 55%±10%, continuous ventilation, and an automatic hour light/dark cycle. Environmental conditions were continuously controlled and recorded. Animals had free access to food and water.

Materials and Methods.

Thirty two female albino Lewis rats were randomly divided into four (4) groups of eight (8) rats. Ocular inflammation was induced at Day 1 by injection of 100 µl of human S-antigen (100 µg) in Freud's complete adjuvant (4 mg/ml) into the footpad of each rat, and an intraperitoneal injection of 1 µg/100 µl pertussis toxin. Disease onset was typically observed between Days 9 and 12 after immunization, and the disease state peaked around Days 16 to 18. The study was halted when at least 60% of the vehicle group showed signs of inflammation.

Beginning on Day 7 until the end of the study, each animal group was treated with a test solution in both eyes as shown in Table 1:

TABLE 1

| Group | Treatment | Frequency |
| --- | --- | --- |
| 1 | 1% Laquinimod | Once Daily (10 µl) |
| 2 | 5% Laquinimod | Once Daily (10 µl) |
| 3 | Vehicle | Once Daily (10 µl) |
| 4 | Cyclosporine A (25 mg/kg) | Once Daily per os (1 ml/kg) |

Both eyes of each rat were examined with a slit-lamp at baseline and then every 2 days from Day 10 to the end of the study. Fifteen minutes prior to each examination, 10 µl of Mydriaticum (0.5% tropicamide) was instilled for papillary dilatation.

Immediately after euthanasia (i.e., at Day 16), both eyeballs of all rats of each group were enucleated and prepared for histological examination. They were fixed in Bouin-Hollande solution, dehydrated, and embedded in paraffin wax. They were then cut into eight sections, approximate five to seven micrometers thick and stained with Trichome of Masson. The retinal thickness and cell infiltration were evaluated and scored using the scale shown in Table 2:

TABLE 2

| | |
| --- | --- |
| No tissue destruction and with any features in a score from 1-7, limited to total destruction of the various layers of the retina | 0 |
| Slight cellular infiltration without destruction of retina | 1 |
| Destruction of the outer segments of rods and cones | 2 |
| Destruction of the outer nuclear layer | 3-4 |
| Destruction of the inner nuclear layer | 5-6 |
| Destruction of the ganglion layer | 7 |

Results.

Animal Body Weight.

Animal body weight was measured and recorded before induction and treatment then at the end of the study. At baseline (treatment), mean body weight per group was between 198 and 202 grams, with a standard deviation of between ±5 grams and 11 grams. At the end of the study (Day 16), mean body weight per group was between 202 grams and 209 grams, with a standard deviation of ±9 grams. There were no relevant differences in body weight between test material, vehicle, and reference animal group.

Ocular Evaluation.

The effect of test material and reference material on ocular inflammation was measured with slit lamp evaluation and scored using the clinical scoring as shown in Table 3:

TABLE 3

| | |
| --- | --- |
| No sign of inflammation, normal iris dilatation after instillation with a mydriatic drug | 0 |
| Discrete inflammation in iris and conjunctiva | 1 |
| Dilatation of iris and conjunctival vessels | 2 |
| Hyperhemia in iris associated with the Tyndall effect in anterior chamber | 3 |
| Same signas as score 3, but add 1 point each if syncehcia, fibrin, or hypopion (cell deposit in the inferior anterior chamber) were observed | 4-6 |

In EAU rats, laquinimod showed a therapeutic effect on ocular inflammation. The 1% laquinimod solution administered once per day reduced intraocular inflammation compared with the vehicle group. The mean clinical score at Day 16 was 1.3±2.1, compared with the vehicle group which was 4.8±1.3. The 5% laquinimod solution administered once per day significantly reduced intraocular inflammation compared with the vehicle group. The mean clinical score at Day 16 was 0.6±1.5 compared with the vehicle group, which was 4.8±1.3. Six out of eight of the rats tested demonstrated no intraocular inflammation. As expected, cyclosporine A, the reference material, administered once per day at 25 mg/kg, demonstrated complete inhibition of intraocular inflammation, with a mean clinical score at Day 16 of 0.0±0.0. Data for the slit lamp test is summarized in Table 4.

Histological examination of the eyeballs revealed that 1% laquinimod administered once per day suppressed uveitis. The mean histologic grade using the scale set forth in paragraph above was 1.2±2.2 versus 5.8±2.3 for the vehicle group. Only four eyes out of sixteen showed a significant destruction of the retina associated with infiltration of inflammatory cells. The 5% laquinimod administered once per day significantly reduced posterior uveitis as assessed by histological grading. The mean histologic grade for this group was 0.7±1.9. Only two eyes (from two different animals) out of sixteen showed a destruction of the retina associated with infiltration of inflammatory cells. As expected, the mean histologic grade for cyclosporine A (25 mg/kg) once per day was 0.0±0.0, thereby totally protecting the retina from destruction. Summary data from the histological evaluation is shown in Table 5.

The 1% and 5% laquinimod solutions reduced the clinical signs of ocular inflammation. The reduced EAU clinical scores correlated well with the decrease in the retinal damage and immune cell infiltration as assessed by histology.

TABLE 4

Slit Lamp Ocular Evaluation of Both Eyes in Albino Rats.

| Treatment | | Baseline | Day 10 | Day 12 | Day 14 | Day 16 |
|---|---|---|---|---|---|---|
| 1% | Mean | 0.0 | 0.1 | 0.1 | 0.8 | 1.3 |
| Laquinimod | SD | 0.0 | 0.3 | 0.3 | 1.8 | 2.1 |
| | Incidence % | 0.0 | 6.3 | 6.3 | 18.8 | 31.3 |
| 5% | Mean | 0.0 | 0.0 | 0.0 | 0.3 | 0.6 |
| Laquinimod | SD | 0.0 | 0.0 | 0.0 | 1.3 | 1.5 |
| | Incidence % | 0.0 | 0.0 | 0.0 | 6.3 | 12.5 |
| Vehicle | Mean | 0.0 | 0.1 | 0.3 | 2.4 | 4.8 |
| (sterile water) | SD | 0.0 | 0.5 | 1.0 | 2.3 | 1.3 |
| | Incidence % | 0.0 | 6.3 | 6.3 | 56.3 | 93.8 |
| Cyclosporine A | Mean | 0.0 | 0.0 | 0.0 | 0.0 | 0.0 |
| (25 mg/kg/day) | SD | 0.0 | 0.0 | 0.0 | 0.0 | 0.0 |
| per os | Incidence % | 0.0 | 0.0 | 0.0 | 0.0 | 0.0 |

TABLE 5

Histological Ocular Evaluation of Both Eyes in Albino Rats.

| Treatment | | Day 16 |
|---|---|---|
| 1% Laquinimod | Mean | 1.2 |
| | SD | 2.2 |
| 5% Laquinimod | Mean | 0.7 |
| | SD | 1.9 |
| Vehicle (sterile water) | Mean | 5.8 |
| | SD | 2.3 |
| Cyclosporine A (25 mg/kg/day) per os | Mean | 0.0 |
| | SD | 0.0 |

Example 2: Evaluation of Ocular Active Anaphylaxis Reduction Following Topical Ocular Administration of Laquinimod in Mice (Late Phase) Using Ovalbumin Model General.

Laquinimod solutions were prepared as in Example 1.

Animals and Animal Husbandry.

Forty (40) male Balb/c albino mice were used for this experiment. The mice were about 7-8 weeks old upon ordering, and were held in observation for at least three (3) days to monitor for signs of ill health or ocular abnormalities. Only healthy animals were accepted for use in this study. The rats were housed under identical environmental conditions, with a relative humidity of 55%±10%, continuous ventilation, and an automatic 12 hour light/dark cycle. Environmental conditions were continuously controlled and recorded. Animals had free access to food and water.

Materials and Methods.

Forty (40) Balb/c albino mice were randomly allocated to five groups of eight animals each. Only the right eyes of each animal were used in this study. Animals were grouped as shown in Table 6:

TABLE 6

| Group | Treatment | Sensitize/Challenge |
|---|---|---|
| 1 | Vehicle (sterile water) | No |
| 2 | Vehicle (sterile water) | Yes |
| 3 | 1% Laquinimod | Yes |
| 4 | 5% Laquinimod | Yes |
| 5 | 1% Prednisolone | Yes |

Sensitization.

On Days 1 and 8, animals in groups 2-5 were injected once intraperitoneally with 0.2 ml of a mixture comprising 5 µg/ml ovalbumin and 15 mg/ml alum in phosphate buffered saline (PBS; pH 7.3-7.4). Animals of group 1 received a mock sensitization comprising 0.2 ml intraperitoneal injection of PBS only on Days 1 and 8.

Treatment Regimen.

Laquinimod or controls were delivered into the right conjunctival sac as follows:

From Day 8 to Day 17, animals were dosed four times daily with 10 µl of either 1% laquinimod, 5% laquinimod, or vehicle. Reference Group 5 was dosed with the same regimen, but starting on Day 15. (**Note: Due to a technical error, four mice from Group 1 (negative vehicle) were not dosed on Day 8 and one mouse from Group 1 (negative vehicle) was not dosed on Day 11. This was deemed not to be a critical error that would affect the outcome of the study so the study was continued).

On Day 18, animals were dosed five times during a three hour period before the second challenge (3 h, 2 h, 1 h, 40 min., and 10 min.).

Challenge.

Allergic conjunctivitis was achieved by a single administration on Day 15 (30 minutes before the treatment regimen) and Day 18 (2 hours after 40 minute treatment) with 10 µl of 5 mg/ml ovalbumin in PBS, pH 7.3-7.4 to the right eyes of all rats in groups 2 through 5. Group 1 was mock challenged with 10 µl PBS only.

On Day 19 (12 h to 24 h after challenge), rats were euthanized using an intraperitoneal injection of pentobarbital. Right eyelids and eyeballs were immediately fixed in Bouin-Hollande solution for 24 hours and embedded in paraffin wax. Fixed samples were cut vertically into 5 to 7 micrometer thick sections with a microtome in two different regions—the bulbar conjunctiva and the fornix and palpebral conjunctiva. Three sections per region were selected for analysis based on the quality of the sectioning. The selected sections were stained with May-Grunwald/acid Giemsa.

After staining, digital images using 200× magnifications were taken with a Leica light microscope. Total area of subconjunctival tissue was measured automatically using the Leica Application Suite (LAS) software. Eosinophils were counted throughout the whole conjunctiva in each of the three sections per sample. The density per square millimeter of eosinophils stained with acid Giemsa was calculated for each specimen. The average cell density per eye was calculated from the results of the six sections.

Results.

Animal Body Weight.

All animals showed normal body weight variation during the study, except for Group 5 (prednisolone), which showed a slight body weight loss between Day 15 and Day 19 (about −4%). This weight loss is commonly observed during chronic corticosteroid treatments. Vehicle groups 1 and 2 showed a 2% and 3% weight gain, respectively, while treatment groups 3 and 4 showed a 4% and 1% weight gain, respectively.

Evaluation of Eosinophil Infiltration.

Conjunctival challenge with ovalbumin in sensitized mice triggers a late phase reaction of anaphylaxis characterized by eosinophil infiltration into the subconjunctival tissue. Eosinophil densities are summarized in Table 7:

TABLE 7

| Treatment | Eosinophil density | | Inhibition of Eosinophil Infiltration vs. Vehicle |
|---|---|---|---|
| | | Density (cells/mm2) | |
| 1% Laquinimod | Mean | 117.5 | 48% |
| | SD | 112.3 | |
| 5% Laquinimod | Mean | 72.5 | 68% |
| | SD | 57.6 | |
| Pred Forte ® Reference | Mean | 23.1 | 90% |
| | SD | 16.9 | |
| Vehicle (sterile water) positive control | Mean | 225.4 | — |
| | SD | 188.4 | |
| Vehicle (sterile water) negative control | Mean | 47.1 | — |
| | SD | 16.0 | |

Topical ocular challenge with ovalbumin in sensitized mice induced a late phase reaction characterized by a significant eosinophil infiltration in to the conjunctival tissues. As shown above, topical administration of 1% prednisolone induced a significant decrease by 90% of the eosinophil density, with a Mann & Whitney-U test p value of 0.0008. Multiple topical administrations of 1% laquinimod reduced eosinophil density by 48% in comparison with positive control; however, this could not be shown to be statistically significant. Multiple topical administrations of 5% laquinimod showed a statistically significant 68% reduction in eosinophil density over the vehicle group, with a Mann & Whitney-U test p value of 0.0023.

Conclusion.

Under experimental conditions, multiple topical administrations of laquinimod inhibited the late ocular anaphylaxis reaction in mice, with a statistically significant effect at a dose of 5%. No adverse clinical effect was observed in laquinimod-treated mice.

Example 3: Dose Conversion Between Species

The National Institutes of Health (NIH) provides a table of Equivalent Surface Area Dosage Conversion Factors below (Table 8) which provides conversion factors that account for surface area to weight ratios between species.

TABLE 8

Equivalent Surface Area Dosage Conversion Factors

| | | To | | | | |
|---|---|---|---|---|---|---|
| | | Mouse 20 g | Rat 150 g | Monkey 3 kg | Dog 8 kg | Man 60 kg |
| FROM | Mouse | 1 | ½ | ¼ | ⅙ | 1/12 |
| | Rat | 2 | 1 | ½ | ¼ | 1/7 |
| | Monkey | 4 | 2 | 1 | ⅗ | ⅓ |
| | Dog | 6 | 4 | 1⅔ | 1 | ½ |
| | Man | 12 | 7 | 3 | 2 | 1 |

In the examples 4-9 below, the administration of the composition is once daily. The administration can be repeated daily for a period of one, two, three or four days, up to 14 days, or longer as necessary.

Example 4: Laquinimod for Treating Uveitis

A laquinimod composition as described herein is administered to the eye of a subject suffering from uveitis. The administration of the composition is effective to treat the subject suffering from uveitis. The administration of the composition is also effective to reduce intraocular inflammation in the subject. The administration of the composition is also effective to reduce retina tissue destruction in the subject.

Example 5: Laquinimod for Treating Bacterial Conjunctivitis

A laquinimod composition as described herein is administered to a subject suffering from bacterial conjunctivitis. The administration of the composition is effective to treat the subject suffering from bacterial conjunctivitis. The administration of the composition is also effective to reduce intraocular inflammation in the subject.

Example 6: Laquinimod for Treating Viral Conjunctivitis

A laquinimod composition as described herein is administered to a subject suffering from viral conjunctivitis. The administration of the composition is effective to treat the subject suffering from viral conjunctivitis. The administration of the composition is also effective to reduce intraocular inflammation in the subject.

Example 7: Laquinimod for Treating Inflammation in the Eye

A laquinimod composition as described herein is administered to a subject suffering from an inflammation of the orbital tissue, the lacrimal apparatus, the eyelid, the cornea, the retina or the optic pathway in the eye. The administration of the composition is effective to treat the subject suffering from the inflammation. The administration of the composition is also effective to reduce intraocular inflammation in the subject.

Example 8: Laquinimod for Treating Allergic Conjunctivitis

A laquinimod composition as described herein is administered to a subject suffering from allergic conjunctivitis at 0.2 mg-0.5 mg laquinimod/day. The administration of the composition is effective to treat the subject suffering from allergic conjunctivitis. The administration of the composition is also effective to reduce intraocular inflammation in the subject. The administration of the composition is also effective to inhibit late ocular anaphylaxis in the subject. The administration of the composition is also effective reduce eosinophil infiltration into the conjunctiva of the subject.

Example 9: Laquinimod for Treating OID

A laquinimod composition as described herein is administered to a subject suffering from an OID. The administration of the composition is effective to treat the subject suffering from the OID. The administration of the composition is also effective to reduce intraocular inflammation in the subject.

Example 10: Comparing Ocular and Oral Administration of Laquinimod for Treating Uveitis Methods.

Laquinimod eye drops (1% and 5%) and oral laquinimod (OD) daily (QD) were administered to albino rats. The animals were dosed for 7 days once 30-40% of the animals have developed the disease. Cyclosporine (PO, QD) was used as positive control.

Disease was induced as follows: Day 1, 100-μL human S-antigen (100 μg in Freud's complete adjuvant (4 mg/mL H37Ra)) injection in footpad+1 μg/100 μL pertussis toxin intraperitoneal injection.

Results.

Response to treatment were assessed by clinical score based on the following scale:

0—No sign of inflammation, normal iris dilatation after instillation with a mydriatic drug.

1—Discrete inflammation in iris and conjunctiva.

2—Dilatation of iris and conjunctival vessels.

3—Hyperhemia in iris associated or not with the Tyndall effect in anterior chamber.

4-7—+1 point was added if synechia, myosis, fibrin, or hypopion (cell deposit in the inferior anterior chamber) were observed.

Results are summarized in Table 9 below:

| Dose | % Inhibition of clinical score on Day 16 |
| --- | --- |
| CyA | 74% |
| 1% PO Laquinimod | 24% |
| 5% PO laquinimod | 39% |
| 1% Laquinimod eye drops | −75% |
| 5% Laquinimod eye drops | 31% |

Results for Histological analysis is shown in Table 10 below:

| Treatment | | Histological ocular evaluation (scale 0-7) Both Eyes/Day 19 | % Inhibition |
| --- | --- | --- | --- |
| Vehicle (1×/day for 7 days; 1 mL/kg; per os) | Mean SD | 3.0 1.6 | N/A |
| Laquinimod (1%; 1× 10 μl instillation/day for 7 days in both eyes) | Mean SD | 2.8 1.5 | 7.00% |
| Laquinimod (5%; 1× 10 μl instillation/day for 7 days in both eyes) | Mean SD | 1.8 1.7 | 40.00% |
| Laquinimod (1%; 1×/day for 7 days; 1 mL/kg; per os) | Mean SD | 2.3 1.7 | 23.00% |
| Laquinimod (5%; 1×/day for 7 days; 1 mL/kg; per os) | Mean SD | 1.2 1.6 | 60.00% |
| Cyclosporin A (1×/day for 7 days; 25 mg/kg/day; per os) | Mean SD | 1.3 1.7 | 57.00% |

REFERENCES

1. U.S. Pat. No. 6,077,851, issued Jun. 20, 2000 (Bjork et al).
2. U.S. Patent Application Publication No. 2005/0192315, published Sep. 1, 2005 (Jansson et al.).
3. PCT International Application Publication No. WO 2005/074899, published Aug. 18, 2005 (Jansson et al.).
4. "Ophthalmologic Disorders" *The Merck Manual*, 17th ed. Mark H. Beers, M D, Robert Berkow, M D, eds. Whitehouse Station, N.J.: Merck Research Labs, 1999.
5. Foster C S (2003) "Ocular Inflammatory Disease: The Importance of Aggressive Therapy", Highlights of the American Academy of Ophthalmology 2003 Annual Meeting—Medscape Education.
6. Gordon (2006) "Orbital inflammatory disease: a diagnostic and therapeutic challenge", Nature, 20:1196-1206.
7. Mishra et al. (2011) "Recent Patents and Emerging Therapeutics in the Treatment of Allergic Conjunctivitis", *Recent Pat Inflamm Allergy Drug Discov.* 2011 January; 5(1):26-36.
8. Rothova et al. (1992) "Uveitis and systemic disease", British Journal of Ophthalmology, 76:137-141.
9. Sergott (2011) "Oral MS Medication May Increase Risk Of Macular Edema In Some Patients", *Ocular Surgery News U.S. Edition*. Sep. 10, 2011.
10. Shah et al. (1992) "Low-dose Methotrexate Therapy For Ocular Inflammatory Disease", *Ophthalmology.* 1992 September; 99(9):1419-23.
11. The Merck Manual, Seventeenth Edition. (1999) Ed. Mark H. Beers and Robert Berkow, Published by Merck Research Laboratories, Whitehouse Station, N.J.
12. "Optometric Clinical Practice Guideline—Care of the Patient with Conjunctivitis", American Optometric Association, 1995, 2002, 243 N. Lindbergh Blvd., St Louis, Mo. 63141-7881.

What is claimed is:

1. A method of treating a subject suffering from an ocular inflammatory disease, the method comprising periodic administration to the subject of a therapeutically effective amount of laquinimod or a pharmaceutically acceptable salt thereof effective to treat the subject, wherein the subject does not have Crohn's disease, and wherein the ocular inflammatory disease is uveitis.

2. The method of claim 1, wherein the therapeutically effective amount of laquinimod is effective to reduce a symptom of the ocular inflammatory disease in the subject, induce a clinical response, induce or maintain clinical remission, inhibit disease progression, inhibit a disease complication, reduce intraocular inflammation, or reduce retina tissue destruction in the subject.

3. The method of claim 1 or 2, wherein the therapeutically effective amount of laquinimod or pharmaceutically acceptable salt thereof is effective to reduce a symptom of uveitis in the subject.

4. The method of claim 1 or 2, wherein the uveitis is anterior uveitis, intermediate uveitis, posterior uveitis, or diffuse uveitis.

5. The method of claim 1 or 2, wherein the laquinimod or pharmaceutically acceptable salt thereof is administered in the form of a liquid or a gel.

6. The method of claim 5, wherein the concentration of laquinimod or pharmaceutically acceptable salt thereof in the liquid or gel is 5-100 mg/ml solution.

7. The method of claim 6, wherein the concentration of laquinimod or pharmaceutically acceptable salt thereof is 10-15 mg/ml solution.

8. The method of claim 1 or 2, wherein the therapeutically effective amount of laquinimod or pharmaceutically acceptable salt thereof is 0.05-4.0 mg per administration.

9. The method of claim 8, wherein the therapeutically effective amount of laquinimod or pharmaceutically acceptable salt thereof is 0.05-2.0 mg per administration.

10. The method of claim 9, wherein the therapeutically effective amount of laquinimod or pharmaceutically acceptable salt thereof is about 0.1 mg per administration.

11. The method of claim 9, wherein the therapeutically effective amount of laquinimod or pharmaceutically acceptable salt thereof is about 0.5 mg per administration.

12. The method of claim 1 or 2, wherein the therapeutically effective amount of laquinimod or pharmaceutically acceptable salt thereof is at least 0.2 mg/day.

13. The method of claim 12, wherein the therapeutically effective amount of laquinimod or pharmaceutically acceptable salt thereof is effective to reduce a symptom of uveitis in the subject.

14. The method of claim 12, wherein the laquinimod or pharmaceutically acceptable salt thereof is administered in the form of a liquid or a gel.

15. The method of claim 14, wherein the concentration of laquinimod or pharmaceutically acceptable salt thereof in the liquid or gel is 20-100 mg/ml solution.

16. The method of claim 15, wherein the concentration of laquinimod or pharmaceutically acceptable salt thereof is 20-50 mg/ml solution.

17. The method of claim 12, wherein the therapeutically effective amount of laquinimod or pharmaceutically acceptable salt thereof is 0.2-4.0 mg per administration.

18. The method of claim 17, wherein the therapeutically effective amount of laquinimod or pharmaceutically acceptable salt thereof is 0.2-2.0 mg per administration.

19. The method of claim 18, wherein the therapeutically effective amount of laquinimod or pharmaceutically acceptable salt thereof is about 0.5 mg per administration.

20. The method of claim 1 or 2, wherein the periodic administration is once per day.

21. The method of claim 1 or 2, wherein the periodic administration is oral administration.

22. The method of claim 1 or 2, wherein the periodic administration is ocular administration.

23. The method of claim 1 or 2, wherein the pharmaceutically acceptable salt of laquinimod is laquinimod sodium.

24. The method of claim 1 or 2, wherein the subject is a human.

25. The method of claim 1, wherein the uveitis is intermediate uveitis, posterior uveitis, or diffuse uveitis.

* * * * *